United States Patent

Sasaoka et al.

[11] Patent Number: 5,977,352
[45] Date of Patent: Nov. 2, 1999

[54] PROCESS FOR PREPARING 3-NORCEPHEM COMPOUNDS

[75] Inventors: Michio Sasaoka, Tokushima; Sigeru Torii, Oakayama-ken; Hideo Tanaka, Okayama; Ryo Kikuchi; Yutaka Kameyama, both of Tokushima, all of Japan

[73] Assignee: Otsuka Kagaku Kabushiki Kaisha, Osaka, Japan

[21] Appl. No.: 09/011,041

[22] PCT Filed: Jun. 9, 1997

[86] PCT No.: PCT/JP97/01994

§ 371 Date: Feb. 6, 1998

§ 102(e) Date: Feb. 6, 1998

[87] PCT Pub. No.: WO97/47627

PCT Pub. Date: Dec. 18, 1997

[30] Foreign Application Priority Data

Jun. 13, 1996 [JP] Japan ................................. 8-175529

[51] Int. Cl.$^6$ ................................................. C07D 501/20
[52] U.S. Cl. ........................................ 540/215; 540/358
[58] Field of Search ............................................ 540/215

[56] References Cited

U.S. PATENT DOCUMENTS 4,081,595  3/1978  Nagata et al. .............................. 544/23
4,634,697  1/1987  Hamashima et al. .................... 514/202

FOREIGN PATENT DOCUMENTS 52-59186   5/1977   Japan.
58-213785  12/1983  Japan.

OTHER PUBLICATIONS

Hideo Tanaka et al., "Synthesis of 2–exo–Methylenepenam and 3–Chloro–Δ$^3$–cephem through a Sequential Reductive 1,2–Eliminations/S-S Bond Fission or Chloride Ion–Addition/Cyclization of 3,4–Disubstituted 2–Butenoates in Metal Salt/Metal Combination", *J. Org. Chem.*, vol. 62, pp. 3610–3617, 1997.

Hideo Tanaka et al., "Construction of cephem framework via sequential reductive 1,2–elimination–hydride addition in a tributyltin hydride–copper(I) chloride–NMP system: systhesis of 3–norcephalosporin", *Chem. Commun.*, pp. 2705–2076, 1996.

*Primary Examiner*—Mark L. Berch
*Attorney, Agent, or Firm*—Kubovcik & Kubovcik

[57] ABSTRACT

The present invention provides a process for preparing 3-norcephem compound represented by the formula (2), characterized in that a hydride reagent is acted on a halogenated β-lactam compound represented by the formula (1) in the presence of a cuprous compound

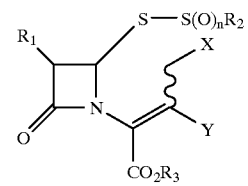

(1)

wherein $R_1$ is a hydrogen atom, amino group or protected amino group, $R_2$ is an aryl or substituted aryl, n is 0 to 2, $R_3$ is a hydrogen atom or carboxylic acid protective group, X is a halogen atom, and Y is a halogen atom or a leaving group

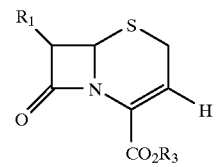

(2)

wherein $R_1$ and $R_3$ are as defined above.

3 Claims, No Drawings

PROCESS FOR PREPARING 3-NORCEPHEM COMPOUNDS

This application is the national stage under 35 U.S.C. § 371 of international application No. PCT/JP97/01994.

TECHNICAL FIELD

The present invention relates to a process for preparing 3-norcephem compounds. The 3-norcephem compounds of the present invention are useful as a starting material of, for example, ceftizoxime that is widely used as an injection medicine (see Handbook of Latest Antibiotics, 9th ed., Yakuho Jihosha Pub. Co., Ltd., pp. 72–73), or ceftibutene that is widely used as an oral medicine (see the aforementioned Handbook, p85), and they are also in widespread commercial use.

BACKGROUND ART

As a process for preparing 3-norcephem compounds represented by the formula (2), there has been reported a process in which a reducing agent, such as zinc powder, is acted on a 3-halocephem compound or 3-sulfonyloxycephem compound represented by the formula (3) (JP-A-59186/1977, Recent Advances in the Chemistry of β-Lactam Antibiotics, p. 170, 1977, Pure & Appl. Chem., 1987, 59, 1041, etc.)

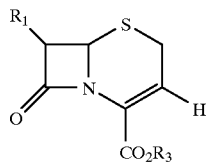

(2)

wherein $R_1$ is a hydrogen atom, amino group or protected amino group, and $R_3$ is a hydrogen atom or carboxylic acid protective group

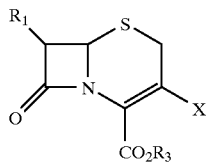

(3)

wherein $R_1$ and $R_3$ are as defined above, and X is a halogen atom, $C_1$–$C_3$ alkanesulfonyloxy group or toluenesulfonyloxy group.

This process is, however, generally not suitable for a commercial process due to the difficulty in preparing 3-halocephem compounds or 3-sulfonyloxycephem compounds, as a starting material.

Also, there has been reported a process for preparing 3-norcephem compounds in which a 3-hydroxycephem compound is subjected to a catalytic hydrogenation to obtain a 3-hydroxycepham, followed by 1,2-elimination using haloformic acid ester/base (see JP-A-213785/1983, JP-A-34714/1983, Pure & Appl. Chem., 1987, 59, 1041, etc.)

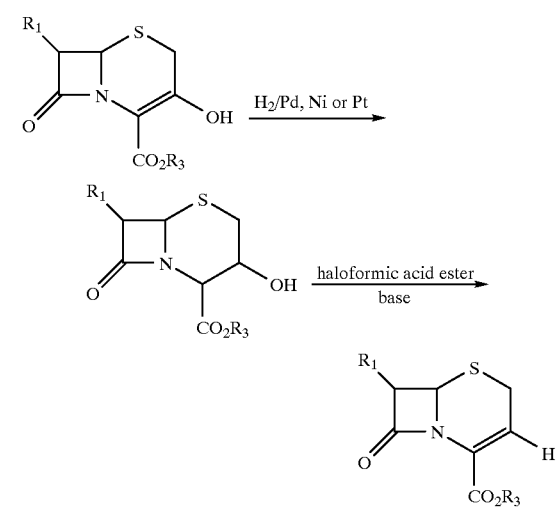

This process is, however, not a commercial process because 3-hydroxycephem whose synthesis is difficult is used as a starting material and further the two steps of catalytic hydrogenation and 1,2-elimination are required.

In addition, Chemistry and Biology of β-Lactam Antibiotics Penicillins and Cephalosporins Volume 1, p. 170, discloses a process in which a 3-formylcephem shown by the following reaction scheme (5) is used as a starting material, and a process employing the Wittig reaction shown by the following reaction scheme (6).

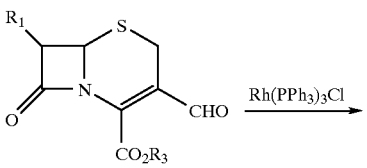

(5)

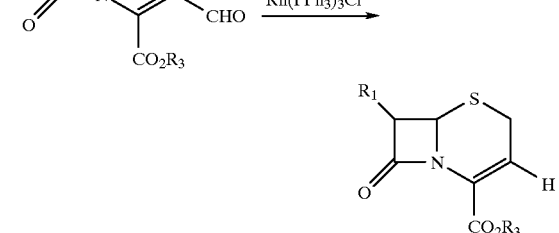

(6)

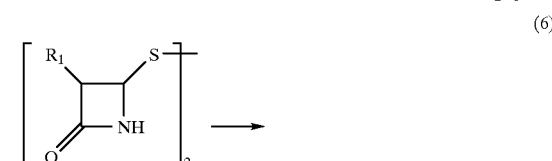
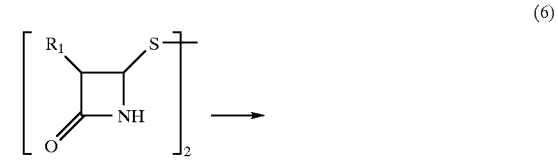
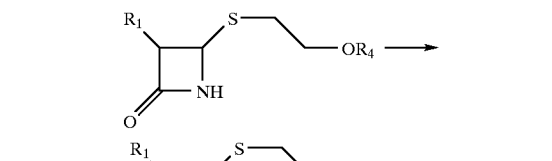
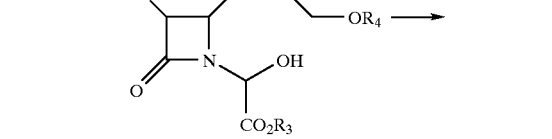
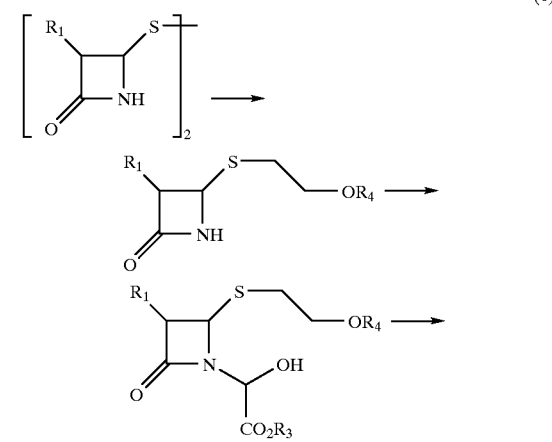

-continued

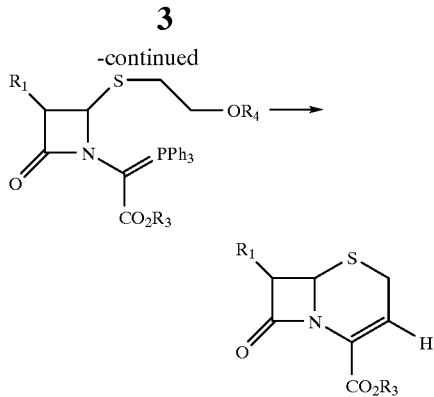

However, the above two processes have difficulties in obtaining their starting materials. In addition, the former requires rhodium complex that is expensive, while the latter has the problem that a large amount of phosphorus-containing waste is formed as a by-product by the Wittig reaction.

An object of the present invention is to overcome the above drawbacks of the conventional processes and provide a process which readily prepares a desired 3-norcephem compound in high yield and purity.

DISCLOSURE OF THE INVENTION

The present invention provides a process for preparing 3-norcephem compound represented by the formula (2), characterized in that a hydride reagent is acted on a halogenated β-lactam compound represented by the formula (1) in the presence of a cuprous compound

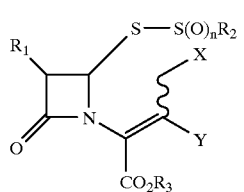
(1)

wherein $R_1$ is a hydrogen atom, amino group or protected amino group, $R_2$ is an aryl or substituted aryl, n is 0 to 2, $R_3$ is a hydrogen atom or carboxylic acid protective group, X is a halogen atom, and Y is a halogen atom or a leaving group

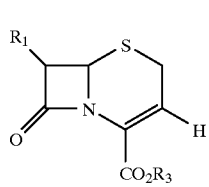
(2)

wherein $R_1$ and $R_3$ are as defined above.

The present invention was accomplished when the present inventor found the outstanding reaction process. Specifically, without employing cephem compounds whose synthesis is difficult, as in the above conventional processes, a desired 3-norcephem compound can be prepared by a single step in which a halogenated β-lactam compound that can be more easily derived from penicillin is used as a starting material, and a specific reagent is acted thereon in the presence of a specific metal compound so that the reduction and cyclization reaction proceed at the same time.

According to the present invention, it is possible to prepare a desired 3-norcephem compound in a reliable manner and a single step which is easier to carry out, and it is also possible to prepare a desired 3-norcephem compound in high yield and purity.

Examples of groups mentioned herein are as follows.

Exemplary of the protected amino represented by $R_1$ are amido groups such as phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, thienylacetamido, phenylacetoxyacetamido, α-oxophenylacetamido, benzamido, p-methylbenzamido, p-methoxybenzamido, p-chlorobenzamido, p-bromobenzamido, phenylglycylamido, phenylglycylamido having protected amino, p-hydroxyphenylglycylamido, p-hydroxyphenylglycylamido having protected amino and/or protected hydroxyl, etc.; imido groups such as phthalimido, nitrophthalimido, etc., in addition to the groups disclosed in Theodora W. Greene, 1981, "Protective Groups in Organic Synthesis" (hereinafter referred to merely as the "literature"), Chap. 7 (pp. 218~287). Examples of protective groups for the amino of phenylglycylamido group and p-hydroxyphenylglycylamido group are those disclosed in the literature, Chap. 7 (pp. 218~287). Examples of protective groups for the hydroxyl of p-hydroxyphenylglycylamido group are those disclosed in the literature, Chap.2 (pp. 10~72).

Examples of aryl and substituted aryl represented by $R_2$ are phenyl, naphthyl, nitrogen-containing heterocyclic group, etc. Exemplary of the nitrogen-containing heterocyclic groups are benzothiazol group, triazol group, thiazol group, tetrazol group, etc. Exemplary of the substituent which may be substituted in the aryl are halogen atoms (such as fluorine atom, chlorine atom, bromine atom, iodine atom), straight-chain or branched $C_1$~$C_4$ alkoxyl groups (such as methoxy, ethoxy), straight-chain or branched $C_1$~$C_4$ alkylthio groups (such as methylthio, ethylthio), straight-chain or branched $C_1$~$C_4$ alkylsulfonyloxy groups (such as methanesulfonyloxy, trifluoromethanesulfonyloxy), aromatic sulfonyloxy or substituted aromatic sulfonyloxy (such as benzenesulfonyloxy, toluenesulfonyloxy), straight-chain or branched $C_1$~$C_4$ alkyl groups (such as methyl, ethyl), amino, amino which has as a substituent one or two straight-chain or branched $C_1$~$C_4$ alkyl groups (such as methylamino, dimethylamino, ethylamino, diethylamino), hydroxyl, acyloxy group represented by RCOO— wherein R is phenyl, tolyl, or straight-chain or branched $C_1$~$C_4$ alkyl group (such as phenylcarbonyloxy, acetyloxy), acyl group represented by RCO— wherein R is as defined above (such as phenylcarbonyl, acetyl), nitro, cyano, phenyl, etc. When the aryl represented by $R_2$ is phenyl group, the aryl may have 1 to 5, especially 1, 2 or 3, same or different groups selected from among the above substituents. When the aryl represented by $R_2$ is naphthyl group, the aryl may have 1 to 7, especially 1, 2 or 3, same or different groups selected from among the above substituents.

Exemplary of the carboxylic acid protecting group represented by $R_3$ are allyl, benzyl, p-methoxybenzyl, p-nitrobenzyl, diphenylmethyl, trichloromethyl, tert-butyl, and those disclosed in the literature, Chap. 5 (pp. 152~192).

Examples of halogen atoms represented by X, Y are fluorine, chlorine, bromine or iodine atom.

Exemplary of the leaving groups represented by Y are lower alkylsulfonyloxy or substituted lower alkylsulfonyloxy (such as methanesulfonyloxy, trifluoromethanesulfonyloxy, trichloromethanesulfonyloxy), aromatic sulfonyloxy or substituted aromatic sulfonyloxy (such as benzenesulfonyloxy, toluenesulfonyloxy), halogenated sulfonyloxy or substituted halogenated sulfonyloxy (such as fluoromethanesulfonyloxy), lower alkylphosphonyloxy or substituted lower alkylphosphoryloxy (such as trimethylphosphoryloxy, triethylphosphoryloxy, tributylphosphopyloxy), aromatic phosphoryloxy or substituted aromatic phosphoryloxy (such as triphenylphosphoryloxy, tritolylphosphoryloxy), etc.

According to the present invention, the 3-norcephem compound of the formula (2) [hereinafter referred to as "3-norcephem compound (2)"] can be prepared by acting a hydride reagent on the above β-lactam halide compound of the formula (1) [hereinafter referred to as "β-lactam halide compound (1)"] in the presence of a cuprous compound.

Any of known cuprous salts is usable as the cuprous compound. Examples thereof are halogenated copper salts such as cuprous chloride (I), cuprous bromide (I), cuprous iodide (I) and cuprous fluoride (I); copper oxides such as cuprous oxide (I). Halogenated copper salt is preferable as cuprous compound. Among these particularly preferable are cuprous chloride (I) and cuprous bromide (I). The cuprous salt may be anhydrous or may contain crystal water. The cuprous salt is used singly or in admixture of at least two of them. The cuprous salt is used in an amount of usually about 1 to about 30 equivalents, preferably about 1 to about 5 equivalents, although not limited specifically, varies widely and is suitably selected.

Examples of hydride reagents are organic tin hydrides (trialkyl tin hydride such as tributyl tin hydride, aromatic tin hydride such as phenyldibutyl tin hydride, alkenyl tin hydride such as vinyldibutyl tin hydride), aluminum hydrides such as lithium aluminum hydride, boron hydrides such as borane, borane-ammonia complex and sodium borohydride, silyl hydride compounds (trialkyl silyl hydrides such as trimethyl silyl hydride, triaryl silyl hydrides such as triphenyl silyl hydride, alkenyl silyl hydrides such as vinyldimethyl silyl hydride), alkali metal hydrides such as lithium hydride and sodium hydride and alkaline earth metal hydrides such as calcium hydride. The hydride reagent is used singly or in admixture of at least two of them. The hydride reagent is used in an amount of usually about 1 to about 30 moles, preferably about 1 to about 10 moles, per mole of the β-lactam halide compound (1).

The reaction is conducted in the presence or absence of solvent with stirring as required, but is preferably conducted in the presence of the solvent. The solvent is not particularly limited unless it causes adverse effect on the reaction. Examples of solvents are lower alkyl esters of lower carboxylic acids such as methyl formate, ethyl formate, propyl formate, butyl formate, methyl acetate, ethyl acetate, propyl acetate, butyl acetate, methyl propionate and ethyl propionate, ketones such as acetone, methyl ethyl ketone, methyl propyl ketone, methyl butyl ketone, methyl isobutyl ketone and diethyl ketone, ethers such as diethyl ether, ethyl propyl ether, ethyl butyl ether, dipropyl ether, diisopropyl ether, dibutyl ether, methyl cellosolve and dimethoxyethane, cyclic ethers such as tetrahydrofuran, dioxane and dioxolan, nitriles such as acetonitrile, propionitrile, butyronitrile, isobutyronitrile and valeronitrile, substituted or unsubstituted aromatic hydrocarbons such as benzene, toluene, xylene, chlorobenzene and anisole, hydrocarbon halides such as dichloromethane, chloroform, dichloroethane, trichloroethane, dibromoethane, propylene dichloride, carbon tetrachloride and Freons, aliphatic hydrocarbons such as pentane, hexane, heptane and octane, cycloalkanes such as cyclopentane, cyclohexane, cycloheptane and cyclooctane, amides such as dimethylformamide, diethylformamide and dimethylacetamide, cyclic amides such as N-methylpyrrolidinone, dimethylsulfoxide, etc. These solvents are used singly or in admixture of at least two of them. These solvents may contain water as required. These solvents are used in an amount of about 10 to about 200 liters, preferably about 20 to about 100 liters, per kilogram of the β-lactam halide compound of the formula (1).

The reaction is conducted usually at −10° C. to 80° C., preferably 0° C. to 50° C. The reaction proceeds satisfactorily at a reaction temperature of around room temperature. Further, when required, the reaction can be conducted within a closed container or in an inert gas such as nitrogen gas. The 3-norcephem compound (2) obtained can be isolated by a usual purification procedure.

The β-lactam compound represented by the formula (1) for use as a starting material of the present invention can be prepared, for example, by acting a halogenating agent or agent for generating a leaving group on the hydroxyl group of the β-lactam compound of the formula "hereinafter referred to as β-lactam compound (4)"

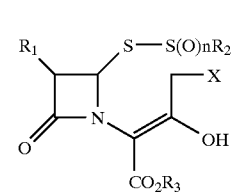

(4)

wherein $R_1$, $R_2$, $R_3$ and X are as defined above, n is 0 to 2.

Examples of useful halogenating agents are phosphorus (V) chlorides such as phosphorus oxychloride and pentachloride, phosphorus (III) chlorides and bromides such as phosphorus trichloride and phosphorus tribromide, triarylphosphine-halogen complexes such as triarylphosphine-dichlorine complex and triarylphosphine-dibromine complex which may have a substituent, mixtures of a triarylphosphine or trialkylphosphine which may have a substituent and a halogen molecule, thionyl halides such as thionyl chloride and thionyl bromide, sulfonyl halides such as sulfonyl chloride and sulfonyl bromide, etc. Usual halogenating agents for the hydroxyl group are usable without any particular limitations. These halogenating agents are used singly or in at least two of them. The agents are used usually in an amount of about 1 to about 50 moles, preferably about 1 to about 10 moles, per mole of the compound of the formula (4). In order to proceed the reaction more effectively, the halogenating agent can be used in combination with an inorganic base such as sodium bicarbonate or sodium carbonate, organic base such as triethylamine, ethyldiisopropylamine or N,N-dimethylaniline, or basic resin such as Amberlite XE-583.

Examples of leaving group generating agents usable are methanesulfonyl chloride, trifluoromethanesulfonyl chloride and like lower alkylsulfonyl chlorides which may have a substituent, benzenesulfonyl chloride, toluenesulfonyl chloride and like aromatic sulfonyl chlorides which may have a substituent, methanesulfonic anhydride, trifluoromethane-sulfonic anhydride and like lower alkylsulfonic anhydrides which may have a substituent, benzenesulfonic anhydride, toluenesulfonic acid anhydride and like aromatic sulfonic anhydrides which may have a substituent, diethylphosphoryl chloride and like lower alkylphosphoryl chlorides which may have a substituent, diphenylphosphoryl chloride and like aromatic phosphoryl chlorides which may have a substituent, etc. Examples of substituents which may be present in these leaving group generating agents are halogen atoms (such as fluorine, chlorine, bromine and iodine atoms), straight-chain or branched $C_1$~$C_4$ alkoxyl groups (such as methoxy, ethoxy), straight-chain or branched $C_1$~$C_4$ alkylthio groups (such as methylthio, ethylthio), straight-chain or branched $C_1$~$C_4$ alkylsulfonyloxy groups (such as methanesulfonyloxy, trifluoromethanesulfonyloxy), straight-chain or branched $C_1$~$C_4$ alkyl groups (such as methyl, ethyl), amino, amino which has as a substituent one or two straight-chain or branched $C_1$~$C_4$ alkyl groups (such as methylamino, dimethylamino, ethylamino, diethylamino), acyloxy group represented by RCOO— wherein R is phenyl, tolyl, or straight-chain or branched $C_1$~$C_4$ alkyl group (such as phenylcarbonyloxy, acetyloxy), acyl group represented by RCO— wherein R is as defined above (such as phenylcarbonyl, acetyl), nitro, cyano, phenyl, etc. The lower alkylsulfonyl chlorides or anhydrides or lower alkylphosphoryl chlorides may have 1 to 5, preferably 1, 2 or 3, such substituents which are different or of the same kind. With regard to aromatic sulfonyl chlorides, aromatic sulfonyl anhydrides and aromatic phosphoryl chlorides, in the case where the aromatic group is phenyl, 1 to 5, preferably 1, 2 or 3, such substituents may be present, or when the aromatic group is naphthyl, 1 to 7, preferably 1, 2 or 3, such substituents may be present. These substituents are different or of the same kind. These leaving group generating agents are used usually in an amount of about 1 to about 50 moles, preferably about 1 to about 10 moles, per mole of the β-lactam compound of the formula (4). The leaving group generating agent can be used in combination with, for example, an inorganic base such as sodium bicarbonate or sodium carbonate, organic base such as triethylamine, ethyldiisopropylamine or N,N-dimethylaniline, or basic resin such as Amberlite XE-583.

This reaction is also conducted in the presence or absence of the solvent with stirring as required, but is preferably conducted in the presence of the solvent. As the solvent is usable those used in the preparation of the 3-norcephem compound (2). The solvent is used in an amount of about 10 to about 200 liters, preferably about 20 to about 100 liters, per kilogram of the β-lactam compound (4). The reaction is conducted usually at −78° C. to 60° C., preferably −40° C. to 30° C.

Altenatively, the compound (4) is acted on with the leaving group generating agent first and then with the halogenating agent, whereby the β-lactam halide compound (1) can be prepared.

In the above, the same leaving group generating agent as above is usable. While the same halogenating agent as above is also usable, other examples of such agents usable for the subsequent reaction include alkali metal halide salts such as lithium chloride and lithium bromide, alkaline earth metal halide salts such as calcium chloride and calcium bromide, and aluminum halide salts such as aluminum chloride and aluminum bromide. The same other conditions as above are usable.

The resulting halogenated β-lactam compound of the formula (1) can be isolated by a usual purification method but can be used in the next reaction without purification.

BEST MODE OF CARRYING OUT THE INVENTION

EXAMPLE 1

A 100 mg of Compound (1a) ($R_1$=PhCH$_2$CONH, $R_2$=Ph, $R_3$=CH$_2$C$_6$H$_4$OCH$_3$-p, X=Cl, Y=Cl, n=2) and 30 mg (2 equivalents) of cuprous chloride were measured out into a 10 ml flask of the egg plant type, and the atmosphere in the flask was replaced by argon gas. After adding 3 ml of N-methyl-pyrrolidinone thereto, 175 μl (4 equivalents) of tributyltin hydride was dropped in all for four times every 30 minutes, followed by stirring for 30 minutes. After the reaction, the reaction mixture was diluted with ethyl acetate and then washed in sequence with 5% hydrochloric acid, water and saturated brine. The obtained organic layer was dried over sodium sulfate and, thereafter, the solvent was distilled off under reduced pressure. The residue was purified by silica gel column chromatography (toluene/ethyl acetate=2/1), to give 59 mg (90%) of Compound (2a). $^1$H-NMR(300 MHz, CDCl$_3$) δ 3.33(dd, J=6.3, 19.2 Hz, 1H), 3.53(dd, J=2.7, 19.2 Hz, 1H), 3.59, 3.71(ABq, J=16.1 Hz, 2H), 3.80(s, 3H), 4.90(d, J=5.1 Hz, 1H), 5.15, 5.22(ABq, J=11.8 Hz, 2H), 5.86(dd, J=5.1, 9.2 Hz, 1H), 6.15(d, J=9.2 Hz, 1H), 6.50(dd, J=2.7, 6.3 Hz, 1H), 6.86~7.35(m, 9H).

EXAMPLE 2

The same reaction as in Example 1 was conducted except that two equivalents of cuprous bromide was used without changing the other reaction conditions. The starting material almost disappeared after three hours and 58 mg (88%) of compound (2a) was obtained. The spectrum data of compound (2a) was fully identical with that of the product of Example 1.

EXAMPLE 3

The same reaction as in Example 1 was conducted except that two equivalents of tributyl tin hydride was used without changing the other reaction conditions. The starting material almost disappeared after three hours and 58 mg (88%) of compound (2a) was obtained. The spectrum data of compound (2a) was fully identical with that of the product of Example 1.

EXAMPLE 4

The same reaction as in Example 1 was conducted except that the reaction was conducted at 45° C. without changing the other reaction conditions. The starting material almost disappeared after two hours and 56 mg (85%) of compound (2a) was obtained. The spectrum data of compound (2a) was fully identical with that of the product of Example 1.

EXAMPLE 5

The same reaction as in Example 1 was conducted except that the reaction was conducted at 3° C. without changing the other reaction conditions. The starting material almost disappeared after two hours and 59 mg (90%) of compound (2a) was obtained. The spectrum data of compound (2a) was fully identical with that of the product of Example 1.

EXAMPLES 6 to 10

The same reaction as in Example 1 was repeated by altering a solvent. Table 1 shows the results.

TABLE 1

| Example | solvent | yield (%) |
| --- | --- | --- |
| 6 | DMF | 87 |
| 7 | DMA | 85 |
| 8 | DMI | 85 |

TABLE 1-continued

| Example | solvent | yield (%) |
|---|---|---|
| 9 | THF | 82 |
| 10 | dioxane | 80 |

EXAMPLE 11

A 100 mg of Compound (1b) ($R_1$=PhCH$_2$CONH, $R_2$=Ph, $R_3$=CHPh$_2$, X=Cl, Y=Cl, n=2) and 29 mg (2 equivalents) of cuprous chloride were measured out into a 10 ml flask of the egg plant type, and the atmosphere in the flask was replaced with argon gas. After adding 3 ml of N-methylpyrrolidinone thereto, 155 ml (4 equivalents) of tributyltin hydride was dropped in all for four times every 30 minutes, followed by stirring for 30 minutes. After the reaction, the reaction mixture was diluted with ethyl acetate and then washed in sequence with 5% hydrochloric acid, water and saturated brine. The obtained organic layer was dried over sodium sulfate and, thereafter, the solvent was distilled off under reduced pressure. The residue was purified by silica gel column chromatography (toluene/ethyl acetate=2/1), to give 64 mg (92%) of Compound (2b). $^1$H-NMR(300 MHz, CDCl$_3$) δ 3.46(dd, J=6.2, 19.0 Hz, 1H), 3.67(dd, J=2.2, 19.0 Hz, 1H), 3.71, 3.79(ABq, J=15.8 Hz, 2H), 5.04(d, J=4.3 Hz, 1H), 6.00(dd, J=4.3, 9.0 Hz, 1H), 6.19(d, J=9.0 HZ, 1H), 6.71(dd, J=2.2, 6.2 Hz, 1H), 7.03(s, 1H), 7.35~7.58 (m, 15H).

EXAMPLE 12

The same reaction as in Example 11 was conducted except that two equivalents of cuprous bromide was used without changing the other reaction conditions. The starting material almost disappeared after three hours and 62 mg (89%) of compound (2b) was obtained. The spectrum data of compound (2b) was fully identical with that of the product of Example 11.

EXAMPLE 13

The same reaction as in Example 11 was conducted except that two equivalents of tributyl tin hydride was used without changing the other reaction conditions. The starting material almost disappeared after three hours and 62 mg (89%) of compound (2b) was obtained. The spectrum data of compound (2b) was fully identical with that of the product of Example 11.

EXAMPLE 14

The same reaction as in Example 1 was conducted except that the starting material was changed to compound (1d) ($R_1$=PhCH$_2$CONH, $R_2$=Ph, $R_3$=CH$_2$C$_6$H$_4$OCH$_3$-p, X=Cl, Y=OSO$_2$CF$_3$, n=2) to obtain 54 mg (94%) of compound (2a). The spectrum data of compound (2a) was fully identical with that of the product of Example 1.

EXAMPLE 15

The same reaction as in Example 11 was conducted except that the starting material was changed to compound (1e) ($R_1$=PhCH$_2$CONH, $R_2$=Ph, $R_3$=CHPh$_2$, X=Cl, Y=OSO$_2$CF$_3$, n=2) to obtain 55 mg (91%) of compound (2b). The spectrum data of compound (2b) was fully identical with that of the product of Example 11.

EXAMPLE 16

The same reaction as in Example 1 was conducted except that the starting material was changed to compound (1f) ($R_1$=PhCH$_2$CONH, $R_2$=Ph, $R_3$=CH$_2$C$_6$H$_4$OCH$_3$-p, X=Cl, Y=OSO$_2$C$_6$H$_4$—CH$_3$-p, n=2) to obtain 50 mg (89%) of compound (2a). The spectrum data of compound (2a) was fully identical with that of the product of Example 1.

EXAMPLE 17

The same reaction as in Example 11 was conducted except that the starting material was changed to compound (1g) ($R_1$=PhCH$_2$CONH, $R_2$=Ph, $R_3$=CHPh$_2$, X=Cl, Y=OSO$_2$C$_6$H$_4$—CH$_3$-p, n=2 to obtain 52 mg (90%) of compound (2b). The spectrum data of compound (2b) was fully identical with that of the product of Example 11.

EXAMPLE 18

The same reaction as in Example 1 was conducted that the starting material was changed to compound (1h) ($R_1$=PhCH$_2$CONH, $R_2$=Ph, $R_3$=CH$_2$C$_6$H$_4$OCH$_3$-p, X=Cl, Y=OSO$_2$CH$_3$, n=2) to obtain 53 mg (86%) of compound (2a). The spectrum data of compound (2a) was fully identical with that of the product of Example 1.

EXAMPLE 19

The same reaction as in Example 11 was conducted except that the starting material was changed to compound (1i) ($R_1$=PhCH$_2$CONH, $R_2$=Ph, $R_3$=CHPh$_2$, X=Cl, Y=OSO$_2$CH$_3$, n=2) to obtain 56 mg (88%) of compound (2b). The spectrum data of compound (2b) was fully identical with that of the product of Example 11.

REFERENCE EXAMPLE 1 (Synthesis of ceftibuten)

The following shows a synthetic route of ceftibuten according to the method disclosed in J. Antibiotics, 1987, XL, 1468, in which ZNH=PhCH$_2$CONH and BH=CHPh$_2$.

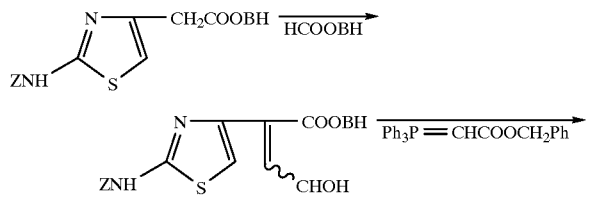

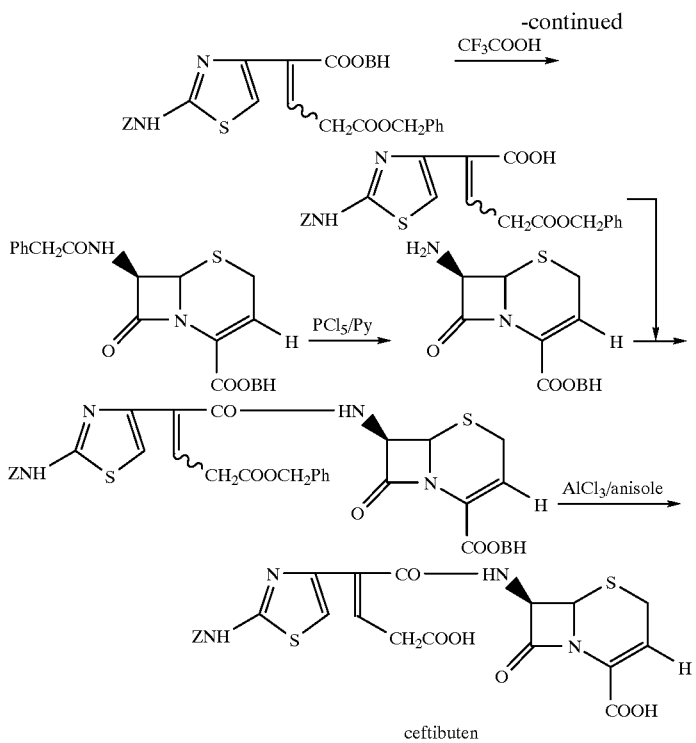

ceftibuten

INDUSTRIAL APPLICABILITY

According to the present invention, it is possible to overcome the drawbacks of the conventional processes and to provide a process which readily prepares a desired 3-norcephem compound in high yield and high purity.

We claim:

1. A process for preparing 3-norcephem compound represented by the formula (2), characterized in that a hydride reagent is reacted with a halogenated β-lactam compound represented by the formula (1) in the presence of a cuprous compound

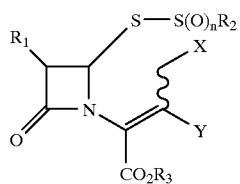

(1)

wherein $R_1$ is a hydrogen atom, amino group or protected amino group, $R_2$ is an aryl or substituted aryl, n is 0 to 2, $R_3$ is a hydrogen atom or carboxylic acid protective group, X is a halogen atom, and Y is a halogen atom or a leaving group

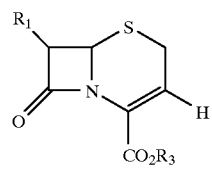

(2)

wherein $R_1$ and $R_3$ are as defined above.

2. A process as defined in claim 1 wherein the cuprous compound is cuprous halide or cuprous oxide.

3. A process as defined in claim 1 wherein the hydride reagent is an organic tin hydride, aluminum hydride, boron hydride, silyl hydride, alkali metal hydride or alkaline earth metal hydride.

* * * * *